US012741003B2

(12) United States Patent
Go et al.

(10) Patent No.: US 12,741,003 B2
(45) Date of Patent: Sep. 22, 2026

(54) COMPOSITION FOR TREATING ALZHEIMER'S DISEASE INCLUDING MIXED EXTRACT OF PINELLIA TUBER, ZIZYPHI FRUCTUS, GLYCYRRHIZA RADIX, GINSENG RADIX, ZINGIBERIS RHIZOMA, SCUTELLARIAE RADIX, AND COPTIDIS RHIZOMA AS ACTIVE INGREDIENT

(71) Applicants: KOREA INSTITUTE OF ORIENTAL MEDICINE, Yuseong-gu (KR); DAEGU GYEONGBUK INSTITUTE OF SCIENCE AND TECHNOLOGY, Dalseong-gun (KR)

(72) Inventors: Younghoon Go, Gyeongsan-si (KR); Buyun Kim, Dong-gu (KR); Jae Kwang Kim, Suseong-gu (KR); Jang-Gi Choi, Dong-gu (KR); Tae Woo Oh, Dong-gu (KR); Malk Eun Pak, Dong-gu (KR); Yeo Jin Park, Dong-gu (KR); Jinsoo Seo, Changnyeong-gun (KR); Hyein Lee, Dong-gu (KR)

(73) Assignees: KOREA INSTITUTE OF ORIENTAL MEDICINE, Yuseong-gu (KR); DAEGU GYEONGBUK INSTITUTE OF SCIENCE AND TECHNOLOGY, Dalseong-gun (KR)

( * ) Notice: Subject to any disclaimer, the term of this patent is extended or adjusted under 35 U.S.C. 154(b) by 241 days.

(21) Appl. No.: 18/697,698

(22) PCT Filed: Sep. 30, 2022

(86) PCT No.: PCT/KR2022/014816
§ 371 (c)(1),
(2) Date: Apr. 1, 2024

(87) PCT Pub. No.: WO2023/055198
PCT Pub. Date: Apr. 6, 2023

(65) Prior Publication Data

US 2025/0064879 A1 Feb. 27, 2025

(30) Foreign Application Priority Data

Sep. 30, 2021 (KR) ........................ 10-2021-0130429

(51) Int. Cl.

| | |
|---|---|
| *A61K 36/00* | (2006.01) |
| *A61K 36/258* | (2006.01) |
| *A61K 36/484* | (2006.01) |
| *A61K 36/539* | (2006.01) |
| *A61K 36/718* | (2006.01) |
| *A61K 36/725* | (2006.01) |
| *A61K 36/8888* | (2006.01) |
| *A61K 36/9068* | (2006.01) |
| *A61P 25/28* | (2006.01) |

(52) U.S. Cl.
CPC .......... *A61K 36/258* (2013.01); *A61K 36/484* (2013.01); *A61K 36/539* (2013.01); *A61K 36/718* (2013.01); *A61K 36/725* (2013.01); *A61K 36/8888* (2013.01); *A61K 36/9068* (2013.01); *A61P 25/28* (2018.01); *A61K 2236/331* (2013.01)

(58) Field of Classification Search
CPC .................................................. A61K 36/258
See application file for complete search history.

(56) References Cited

U.S. PATENT DOCUMENTS

| | | | | |
|---|---|---|---|---|
| 8,182,845 B2 * | 5/2012 | Asaka | .................... | A61K 36/28 424/736 |
| 2004/0185128 A1 | 9/2004 | Kim et al. | | |
| 2010/0330210 A1 | 12/2010 | Asaka et al. | | |
| 2011/0020301 A1 | 1/2011 | Scarpa et al. | | |
| 2020/0196637 A1 | 6/2020 | Asada et al. | | |
| 2021/0252092 A1 | 8/2021 | Joo et al. | | |
| 2022/0265751 A1 | 8/2022 | Sasaki et al. | | |

FOREIGN PATENT DOCUMENTS

| | | | |
|---|---|---|---|
| CN | 105267917 A | 1/2016 | |
| CN | 110841023 A * | 2/2020 | ........... A61K 36/718 |
| JP | H06211680 A | 2/1994 | |

(Continued)

OTHER PUBLICATIONS

Chen et al. "Banxia Xiexin decoction ameliorated cognition via the regulation of insulin pathways and glucose transporters in the hippocampus of APPswe/PSIdE9 mice", International Journal of Immunopathology and Pharmacology, 32, 1-8 (2018).
Narayan et al. "PICALM Rescues Endocytic Defects Caused by the Alzheimer's Disease Risk Factor APOE4," Cell Reports, vol. 33, No. 108224 (2020).
Lim et al. "Screening of 56 Herbal formulas covered by the National Health Insurance Service on Dementia-related Factors", J. Korean Med., 39(3), pp. 1-16 (2018). English abstract included.
Pankratz et al. "Presence of an APOE4 Allele Results in Significantly Earlier Onset of Parkinson's Disease and a Higher Risk With Dementia", Movement Disorders. vol. 21, No. 1, pp. 45-49 (2006).
Xiao, et al. "A network pharmacology-based study on key pharmacological pathways and targets of Qi Fu Yin acting on Alzheimers disease", Experimental Gerontology, vol. 149, pp. 1-17 (2021).

(Continued)

*Primary Examiner* — Qiuwen Mi
(74) *Attorney, Agent, or Firm* — Meunier Carlin & Curfman LLC

(57) ABSTRACT

The present invention relates to a composition for treating, improving, or preventing Alzheimer's disease caused by ApoE4 gene mutation, the composition including Banha-Sasim-Tang as an active ingredient. The composition including Banha-Sasim-Tang as an active ingredient of the present invention and a treatment method exhibit excellent effects of reducing amyloid beta proteins and inhibiting deposition thereof, which are specific to Alzheimer's disease caused by ApoE4 gene mutation, thereby having high applicability as a specific composition for preventing, improving, or treating Alzheimer's disease caused by ApoE4 gene mutation.

7 Claims, 9 Drawing Sheets

Specification includes a Sequence Listing.

(56) References Cited

FOREIGN PATENT DOCUMENTS

| | | | |
|---|---|---|---|
| JP | 6704050 | B2 | 6/2020 |
| KR | 10-2002-0096925 | A | 12/2002 |
| KR | 10-2007-0099144 | A | 10/2007 |
| KR | 10-2010-0126326 | A | 12/2010 |
| KR | 101985965 | B1 | 9/2019 |
| KR | 10-2021-0010354 | A | 1/2021 |
| KR | 10-2209028 | B1 | 1/2021 |
| WO | 2007038610 | A2 | 4/2007 |
| WO | 2007088681 | A1 | 8/2007 |
| WO | 2021025139 | A1 | 2/2021 |

OTHER PUBLICATIONS

Li, et al. “Potential anti-dementia agents in traditional Chinese medicine”, vol. 4, No. 6, pp. 877-886 (2009).

Office Action issued in EP Application No. 22876969.1, dated Sep. 9, 2025, 10 pages.

* cited by examiner

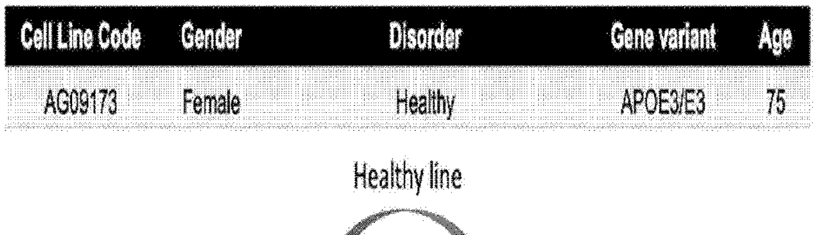
| Cell Line Code | Gender | Disorder | Gene variant | Age |
| --- | --- | --- | --- | --- |
| AG09173 | Female | Healthy | APOE3/E3 | 75 |
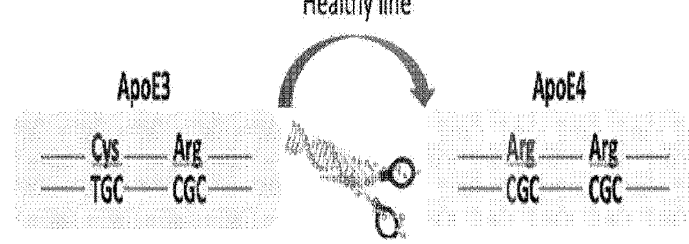
[FIG. 1]
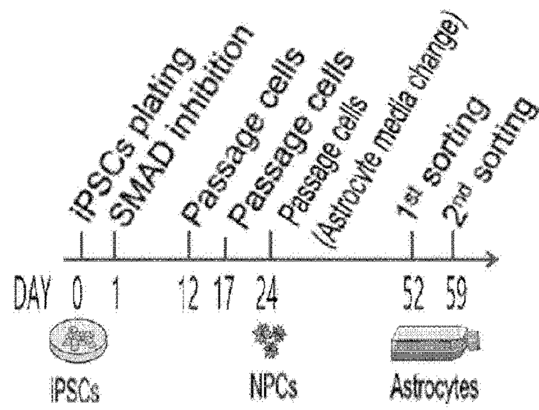
[FIG. 2A]
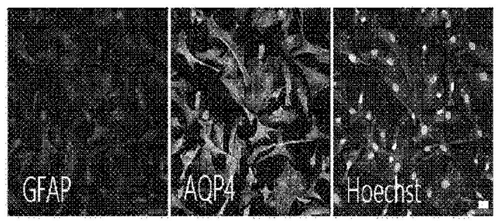
[FIG. 2B]

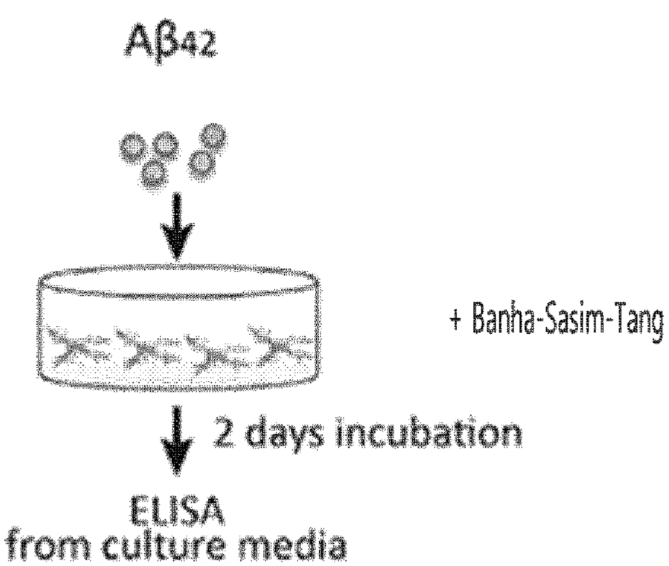
$$A\beta_{42}\ \text{uptake index} = \frac{\text{Reduced levels of } A\beta_{42} \text{ in media}}{\text{The number of cells}}$$
[FIG. 3]

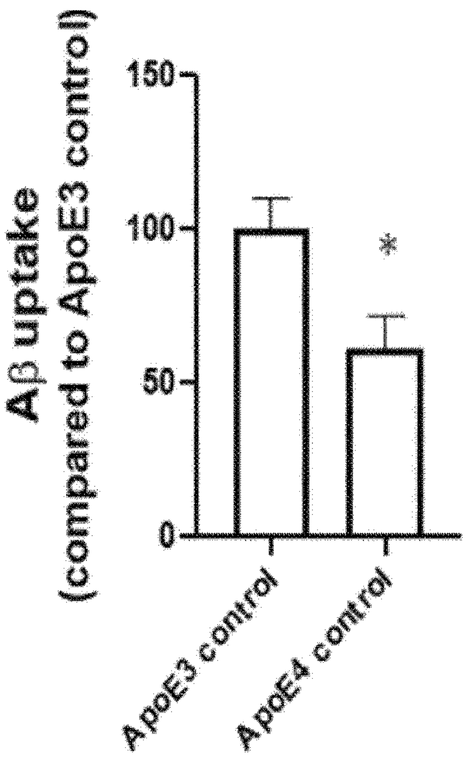
[FIG. 4A]

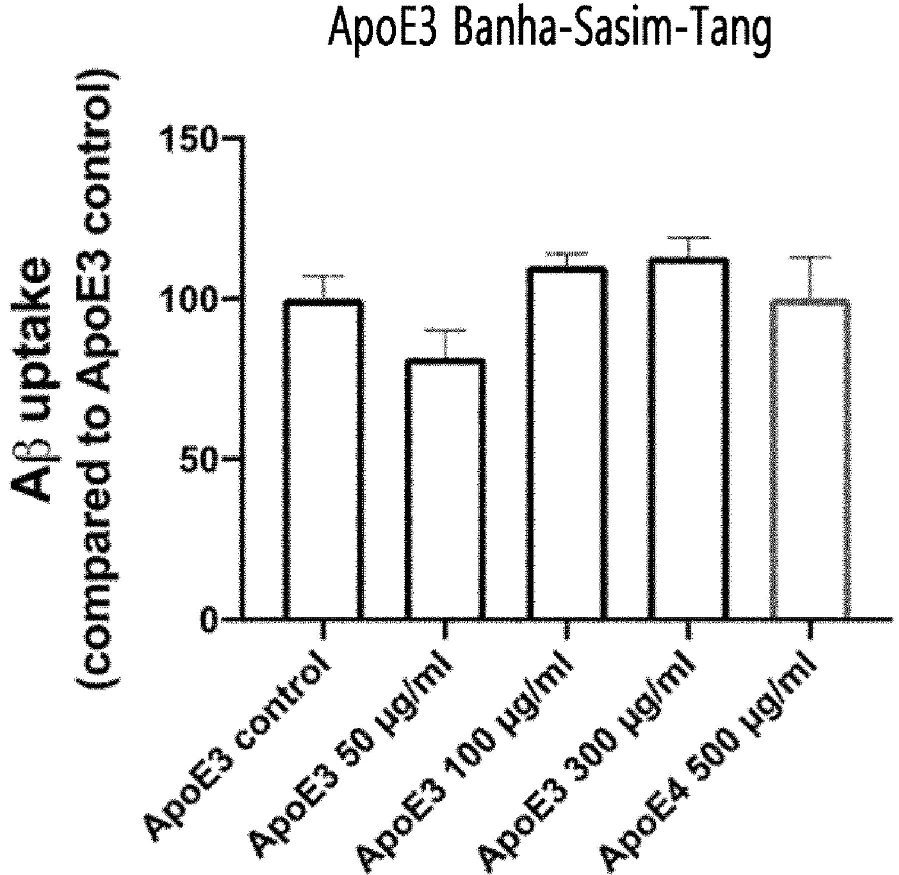
[FIG. 4B]

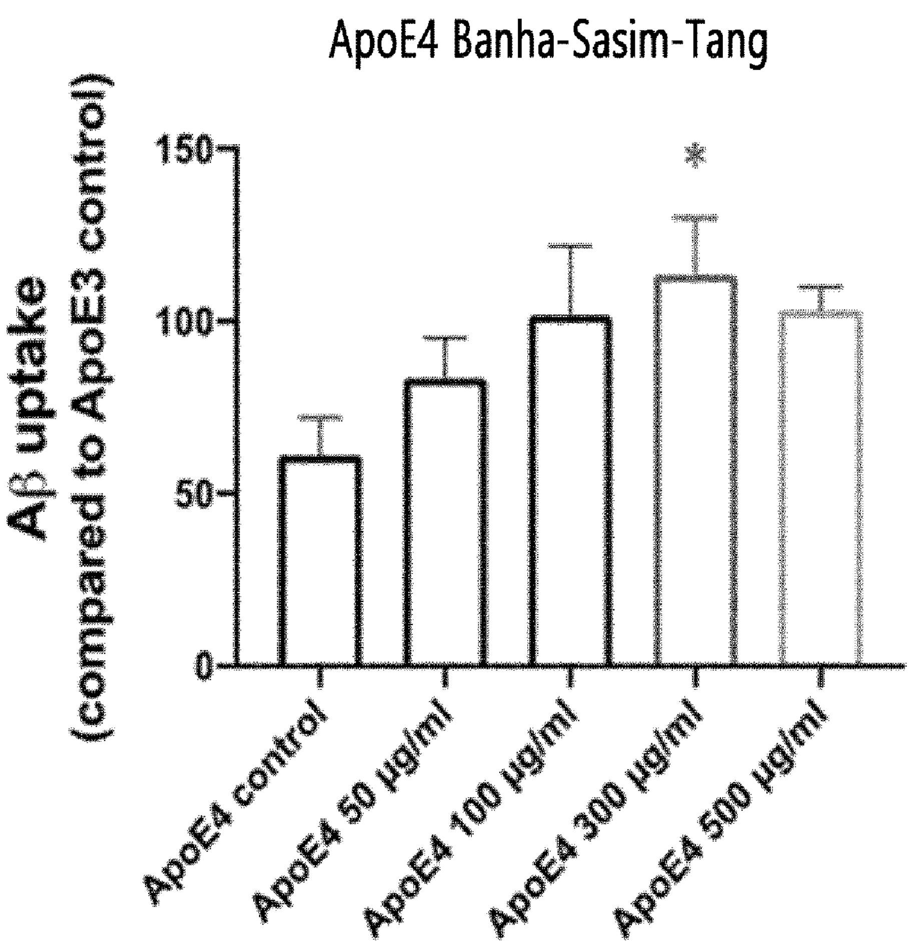
[FIG. 4C]
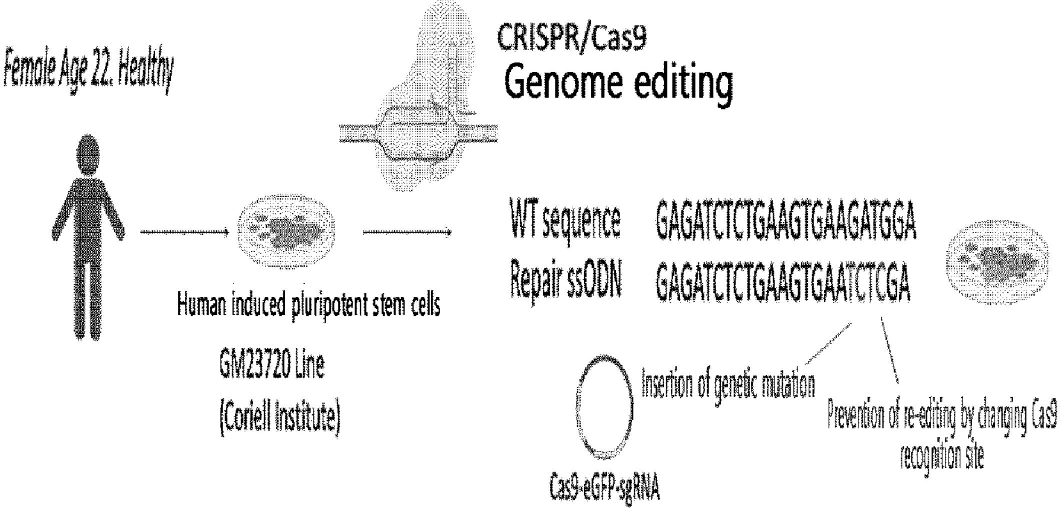
[FIG. 5]

Timeline
- 2 days incubation with 250 ng/ml $A\beta_{1-42}$ oligomer
- Treatment with 300 ug/ml of Banha-Sasim-Tang
[FIG. 6A]
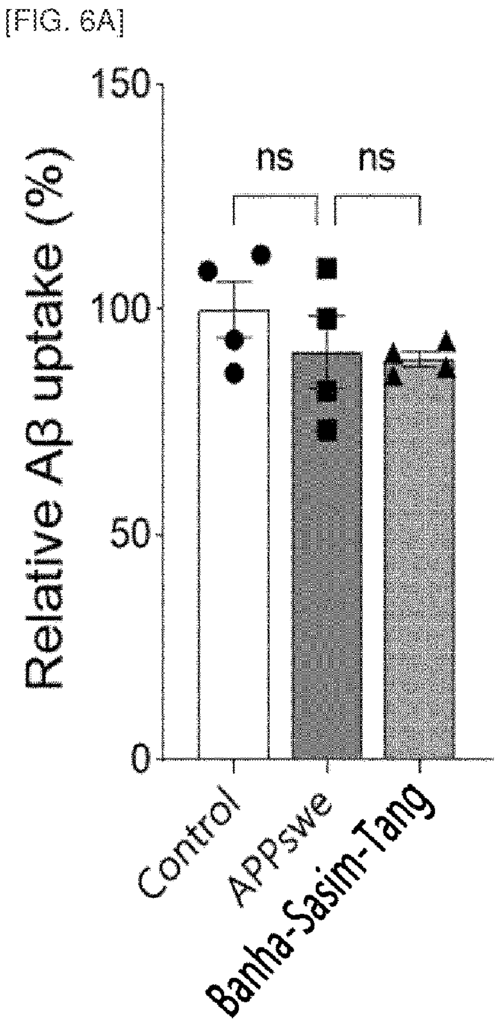
[FIG. 6B]

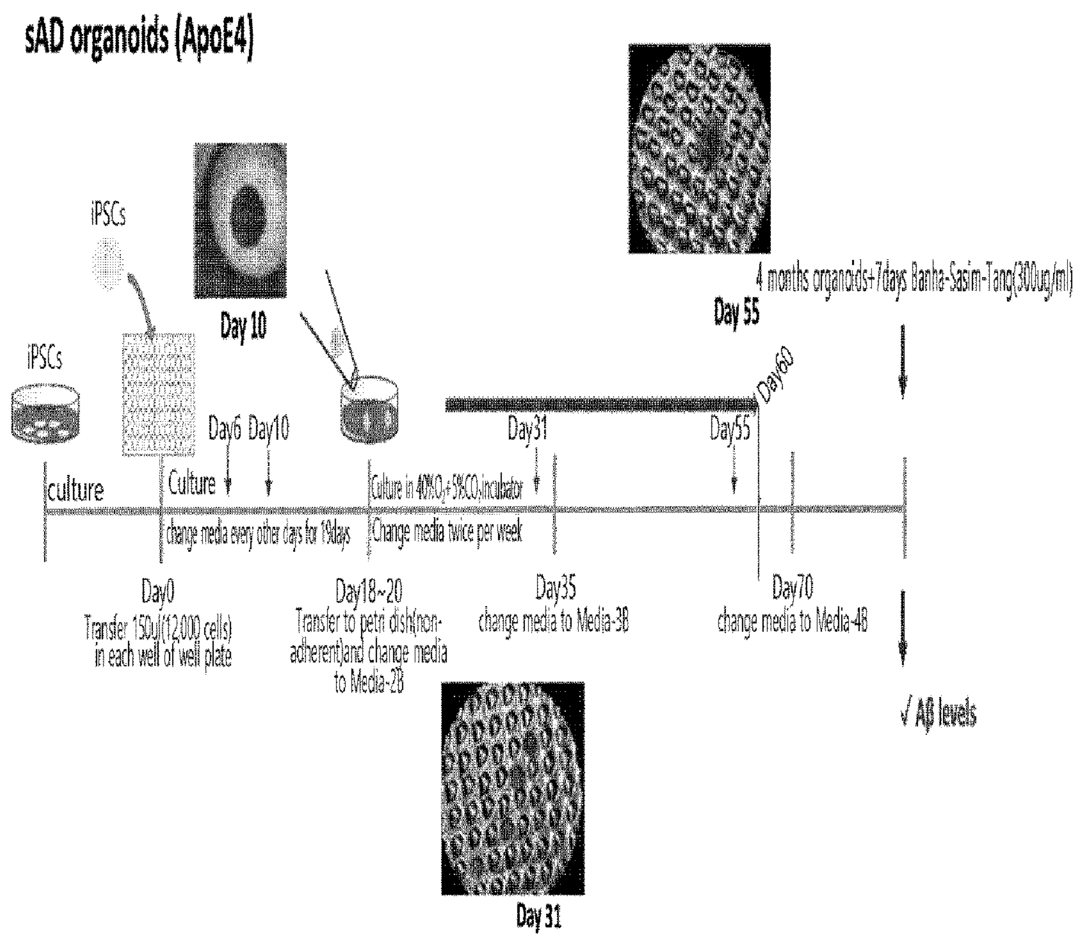
[FIG. 7]

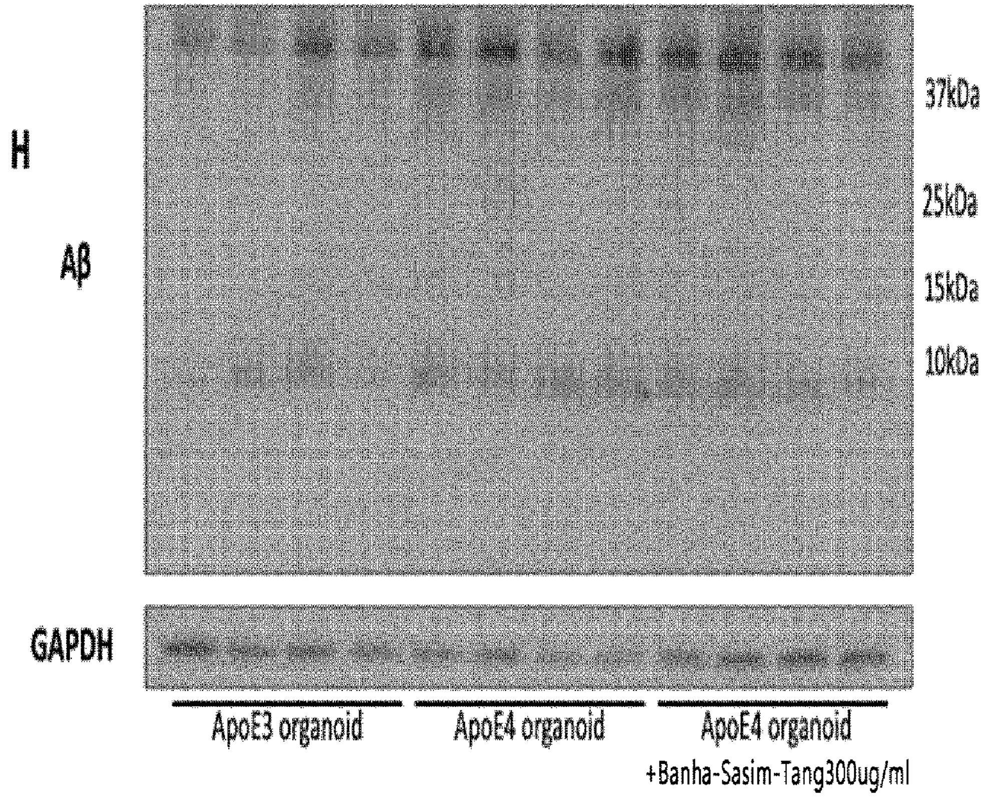
[FIG. 8A]

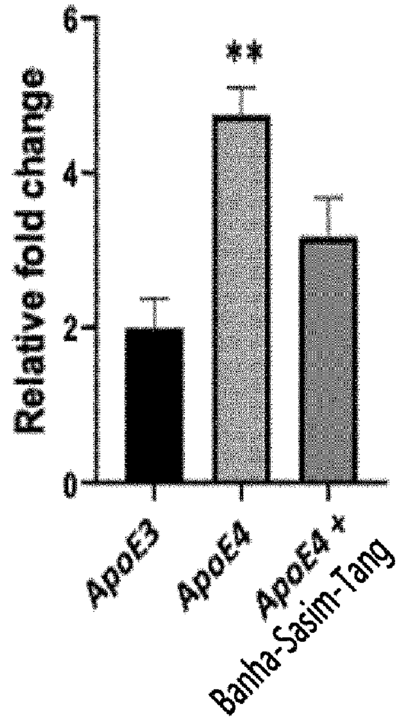
[FIG. 8B]

SEQUENCE LISTING

```
Sequence total quantity: 2
SEQ ID NO: 1             moltype = DNA  length = 23
FEATURE                  Location/Qualifiers
misc_feature             1..23
                         note = Description of sequence: WT sequence
source                   1..23
                         mol_type = genomic DNA
                         organism = Homo sapiens
SEQUENCE: 1
gagatctctg aagtgaagat gga                                           23

SEQ ID NO: 2             moltype = DNA  length = 23
FEATURE                  Location/Qualifiers
misc_feature             1..23
                         note = Description of sequence: Repair ssODN
source                   1..23
                         mol_type = other DNA
                         organism = synthetic construct
SEQUENCE: 2
gagatctctg aagtgaatct cga                                           23
```

COMPOSITION FOR TREATING ALZHEIMER'S DISEASE INCLUDING MIXED EXTRACT OF PINELLIA TUBER, ZIZYPHI FRUCTUS, GLYCYRRHIZA RADIX, GINSENG RADIX, ZINGIBERIS RHIZOMA, SCUTELLARIAE RADIX, AND COPTIDIS RHIZOMA AS ACTIVE INGREDIENT

REFERENCE TO SEQUENCE LISTING

A Sequence Listing conforming to the rules of WIPO Standard ST.26 is hereby incorporated by reference. Said Sequence Listing has been filed as an electronic document via Patent Center encoded as XML in UTF-8 text. The electronic document, created on Aug. 2, 2024, is entitled "11254-010US1_ST26.xml", and is 3,891 bytes in size.

TECHNICAL FIELD

The present invention relates to a pharmaceutical composition for preventing or treating Alzheimer's disease, the pharmaceutical composition including, as an active ingredient, a mixed extract of *Pinellia tuber, Zizyphi fructus, Glycyrrhiza radix, Ginseng radix, Zingiberis rhizoma, Scutellariae radix*, and *Coptidis rhizoma*; a health functional food composition for preventing or improving Alzheimer's disease, the health functional food composition including, as an active ingredient, a mixed extract of *Pinellia tuber, Zizyphi fructus, Glycyrrhiza radix, Ginseng radix, Zingiberis rhizoma, Scutellariae radix*, and *Coptidis rhizoma*; a quasi-drug composition for preventing or improving Alzheimer's disease, the quasi-drug composition including, as an active ingredient, a mixed extract of *Pinellia tuber, Zizyphi fructus, Glycyrrhiza radix, Ginseng radix, Zingiberis rhizoma, Scutellariae radix*, and *Coptidis rhizoma*; or a method of treating Alzheimer's disease, the method including the step of administering the pharmaceutical composition to a subject.

SEQUENCE LISTING

A Sequence Listing conforming to the rules of WIPO Standard ST.26 is hereby incorporated by reference. Said Sequence Listing has been filed as an electronic document via Patent Center encoded as XML in UTF-8 text. The electronic document, created on Sep. 9, 2024, is entitled "11254-010US1_ST26.xml", and is 3,891 bytes in size.

BACKGROUND ART

Alzheimer's disease is a disease in which cognitive functions, including memory, gradually deteriorate, and is the most common degenerative brain disease. The main symptoms of Alzheimer's disease include decline in memory, decreased language skills, a decline in time and space perception, decreased judgment and daily life performance, personality changes, agitated behavior, psychological and behavioral symptoms such as depression delusions, fecal and urinary incontinence, and physical symptoms such as mobility impairment, etc.

The incidence of Alzheimer's disease is continuously increasing worldwide due to the increase in the elderly population according to increased life expectancy. Experts predict that the number of patients suffering from Alzheimer's disease will reach 13.8 million in the United States and 2.37 million in Korea by 2050, and its severity is increasing. Accordingly, studies on the treatment and improvement of Alzheimer's disease are actively conducted around the world.

Meanwhile, it is known that Alzheimer's disease is caused by various mechanisms such as hyperphosphorylation of tau protein, inflammatory response, deposition of beta-amyloid in the brain due to excessive production thereof, and oxidative damage, etc. Although all causes of these mechanisms have not yet been accurately identified, genetic causes are reported to account for approximately 40% to 50% of all Alzheimer's disease cases.

Typically, mutations in the amyloid precursor protein gene and presenilin gene are genetic factors that increase the risk of early-onset Alzheimer's disease, of which symptoms begin under the age of 65, and ApoE4 alleles of the apolipoprotein E gene are known to be a genetic factor that increases the risk of late-onset Alzheimer's disease, of which symptoms usually begin after the age of 65.

As described, Alzheimer's disease is caused by various causes. There has been some research on specific treatments for these specific causes of Alzheimer's disease. For example, Korean Patent Publication No. 10-2010-0126326A discloses a composition including superoxide dismutase and S-adenosylmethionine for the treatment of Alzheimer's disease caused by overexpression of presenilin 1 and BACE. As described, although there are some studies, studies on specific treatments according to the specific causes of Alzheimer's disease have not yet been actively conducted.

ApoE gene refers to a gene encoding a sequence of apolipoprotein E (ApoE). The ApoE gene encodes a structural protein of lipoprotein, which is a normal component of plasma, such as high density lipoprotein (HDL), low density lipoprotein (LDL), and very low density lipoprotein (VLDL), and is located on chromosome 19 and acts as a lipid transport protein, and it is known to play a key role in regulating lipid metabolism after damage to the central and peripheral nervous system. The ApoE gene has three allelic genotypes, E2, E3 and E4. Among the above allelic genotypes, E2 and E4 are known to be associated with Alzheimer's dementia. It is known that the apolipoprotein E4 allele (ApoE4) is a risk factor for the development of Alzheimer's dementia, and the apolipoprotein E2 allele (ApoE2) is a protective factor for the development of Alzheimer's dementia. It is known that approximately 10% to 15% of all Alzheimer's dementia patients develop the disease due to the above-mentioned ApoE4 gene mutation.

As described, the ApoE4 genotype is one of the major causes of Alzheimer's disease, and the present inventors have made intensive efforts to develop a composition having specific activity against Alzheimer's disease caused by ApoE4 gene mutation. As a result, they investigated that a mixed extract (hereinafter, referred to as Banha-Sasim-Tang) of *Pinellia tuber, Zizyphi fructus, Glycyrrhiza radix, Ginseng radix, Zingiberis rhizoma, Scutellariae radix*, and *Coptidis rhizoma* has the effect of reducing amyloid beta specific to ApoE4-induced Alzheimer's disease, and developed the use of Banha-Sasim-Tang in the treatment of Alzheimer's disease caused by ApoE4 gene mutation, thereby completing the present invention.

Prior to this patent application, there was no literature or technology indicating that Banha-Sasim-Tang could be specifically applied to the improvement of Alzheimer's disease caused by ApoE4 gene mutation.

DISCLOSURE

Technical Problem

An object of the present invention is to provide a pharmaceutical composition for preventing or treating Alzheimer's disease, the pharmaceutical composition including, as an active ingredient, a mixed extract of *Pinellia tuber, Zizyphi fructus, Glycyrrhiza radix, Ginseng radix, Zingiberis rhizoma, Scutellariae radix*, and *Coptidis rhizoma.*

Another object of the present invention is to provide a pharmaceutical composition for preventing or treating Alzheimer's disease caused by ApoE4 gene mutation, the pharmaceutical composition including, as an active ingredient, a mixed extract of *Pinellia tuber, Zizyphi fructus, Glycyrrhiza radix, Ginseng radix, Zingiberis rhizoma, Scutellariae radix*, and *Coptidis rhizoma.*

Still another object of the present invention is to provide a health functional food composition for preventing or improving Alzheimer's disease, the health functional food composition including, as an active ingredient, a mixed extract of *Pinellia tuber, Zizyphi fructus, Glycyrrhiza radix, Ginseng radix, Zingiberis rhizoma, Scutellariae radix*, and *Coptidis rhizoma.*

Still another object of the present invention is to provide a quasi-drug composition for preventing or improving Alzheimer's disease, the quasi-drug composition including, as an active ingredient, a mixed extract of *Pinellia tuber, Zizyphi fructus, Glycyrrhiza radix, Ginseng radix, Zingiberis rhizoma, Scutellariae radix*, and *Coptidis rhizoma.*

Still another object of the present invention is to provide a method of treating Alzheimer's disease, the method including the step of administering the composition to a subject excluding humans.

Technical Solution

Each description and embodiment disclosed in this disclosure may also be applied to other descriptions and embodiments. That is, all combinations of various elements disclosed in this disclosure fall within the scope of the present invention. Further, the scope of the present invention is not limited by the specific description described below.

Further, those skilled in the art will recognize, or be able to ascertain using no more than routine experimentation, many equivalents to the specific embodiments of the disclosure described herein. Further, these equivalents should be interpreted to fall within the present invention.

Furthermore, throughout the specification of the present invention, when a part is referred to as "Including" an element, it will be understood that other elements may be further included rather than other elements being excluded unless content to the contrary is specially described.

Hereinafter, the present invention will be described in more detail.

The present invention relates to use of a composition including, as an active ingredient, a mixed extract of *Pinellia tuber, Zizyphi fructus, Glycyrrhiza radix, Ginseng radix, Zingiberis rhizoma, Scutellariae radix*, and *Coptidis rhizome* in preventing, improving, or treating Alzheimer's disease.

To achieve the above object, an aspect of the present invention provides a pharmaceutical composition including, as an active ingredient, a mixed extract of *Pinellia tuber, Zizyphi fructus, Glycyrrhiza radix, Ginseng radix, Zingiberis rhizoma, Scutellariae radix*, and *Coptidis rhizoma.*

As used herein, the term "Banha-Sasim-Tang" refers to a mixed extract of *Pinellia tuber, Zizyphi fructus, Glycyrrhiza radix, Ginseng radix, Zingiberis rhizoma, Scutellariae radix*, and *Coptidis rhizome*, and may be used interchangeably. The Banha-Sasim-Tang may be prepared by a method commonly used in the art. It is known that Banha-Sasim-Tang is generally used in oriental medicine for symptoms such as gastritis, macrogastria, gastroduodenal ulcer, gastroenteritis, etc.

In one embodiment, the Banha-Sasim-Tang may be an extract of a mixture of *Pinellia tuber, Zizyphi fructus, Zingiberis rhizoma, Scutellariae radix, Ginseng radix, Glycyrrhiza radix*, and *Coptidis rhizome*, or a mixture of extracts of the respective components, but is not limited thereto.

In one specific embodiment, a ratio of *Pinellia tuber: Zizyphi fructus:Glycyrrhiza radix:Ginseng radix; Zingiberis rhizoma:Scutellariae radix:Coptidis rhizome* included in the Banha-Sasim-Tang may be about 1.2 to about 2.0:about 0.8 to about 1.2:about 0.8 to about 1.2:about 0.8 to about 1.2:about 0.6 to about 1.0:about 0.8 to about 1.2:about 0.2 to about 0.5, but is not limited thereto.

In another specific embodiment, the Banha-Sasim-Tang may be an extract of a mixture of about 1.2 g to about 2.0 g of *Pinellia tuber*, about 0.8 g to about 1.2 g of *Zizyphi fructus*, about 0.8 g to about 1.2 g of *Glycyrrhiza radix*, about 0.8 g to about 1.2 g of *Ginseng radix*, about 0.6 g to about 1.0 g of *Zingiberis rhizoma*, about 0.8 g to about 1.2 g of *Scutellariae radix*, and about 0.2 g to about 0.5 g of *Coptidis rhizome*, but is not limited thereto.

In one preferred embodiment, the Banha-Sasim-Tang may be an extract of a mixture of about 1.67 g of *Pinellia tuber*, about 1 g of *Zizyphi fructus*, about 1 g of *Glycyrrhiza radix*, about 1 g of *Ginseng radix*, about 0.83 g of *Zingiberis rhizoma*, about 1 g of *Scutellariae radix*, and about 0.33 g of *Coptidis rhizome*, or an extract of a mixed solution with a similar ratio thereto but different weights thereof, but is not limited thereto.

Hereinafter, the components of the Banha-Sasim-Tang will be described in more detail.

As used herein, the term "*Pinellia tuber*" generally refers to the tuber after removing the cork layer from *Pinellia ternata* Breitenbach belonging to the family Araceae. It is also known by names such as Jimun, Yangan-Banha, etc. It is almost odorless and slightly viscous, pungent in taste, and warming in nature. In oriental medicine, *Pinellia tuber* is used for phlegm, cough, and asthma, and may be used for symptoms such as headache caused by sputum, dizziness, chest tightness, fullness, vomiting, sore throat, abscess on the back, mastitis, and vomiting of pregnancy, etc. It is reported that *Pinellia tuber* has pharmacological actions including expectorant action, antitussive action, vomiting sedation, prevention of silicosis, anticancer action, etc.

As used herein, the term "*Zizyphi fructus*" refers to the fruit of the *Zizyphus jujuba* plant, and its scientific name is *Ziziphus jujuba* var. *inermis*. It is also known as Jo or Mokmil. It has a reddish-brown surface, is oval in shape, is 1.5 to 2.5 cm long, and tastes sweet when ripe. In oriental medicine, it is reported that *Zizyphi fructus* is used as a diuretic, tonic, and laxative agent.

As used herein, the term "*Glycyrrhiza radix*" refers to a perennial herbaceous plant belonging to the family Fabaceae, and its scientific name is *Glycyrrhiza uralensis* FISCH. The *Glycyrrhiza radix* is also called Gukro, Micho, Milgam, Milcho, Yeongtong, Cheomcho, Rocho, etc. The husk of *Glycyrrhiza radix* is reddish brown or dark brown in color and has wrinkles in a longitudinal direction. In oriental medicine, it is reported that *Glycyrrhiza radix* is used as a component harmonizing toxicities of drugs to allow the drugs to take effect, controlling chills and fevers, and bad energy in the metacarpus, dilating all blood vessels, and strengthening muscles and bones.

As used herein, the term "*Ginseng radix*" refers to the root of *Ginseng radix Panax ginseng* C. A. Meyer (the family Araliaceae). The *Ginseng radix* is also called by names such as Gwigae, Geumjeongokran, Shincho, Okjeong, Inmi, Inham, Jijeong, Tojeong, Haasam, Heolsam, Heolsam, Hwangsam, Yasansam, and Byeoljiksam, etc. *Ginseng radix* has a unique odor, tastes sweet and slightly bitter, and is warm in nature. In oriental medicine, it is reported that *Ginseng radix* is used to recover vitality, to treat physical weakness, weariness, fatigue, loss of appetite, vomiting, and diarrhea, and to enhance a renal function.

As used herein, the term "*Zingiberis rhizoma*" refers to the dried rhizome of *Zingiber officinale* Roscoe. *Zingiberis rhizoma* is also called Baekgang or Gyungang. It has a unique odor and pungent and hot in nature. *Zingiberis rhizoma* has pharmacological effects such as anti-inflammatory, analgesic, and antibacterial actions, etc.

As used herein, the term "*Scutellariae radix*" refers to the root of *Scutellaria baicalensis* belonging to the genus *Scutellaria*, the family Lamiaceae, either intact or without the periderm. *Scutellariae radix* is almost odorless and slightly bitter in taste. It is reported that *Scutellariae radix* has pharmacological effects such as anticancer, liver protection, and antioxidant effects.

As used herein, the term "*Coptidis rhizoma*" refers to an evergreen perennial herb of the dicotyledonous plant belonging to the family Ranunculaceae, the order Ranunculaceae. The scientific name of *Coptidis rhizoma* is Cop #s *chinensis*, and is bitter in taste and cold in nature. Berberine, which is the main ingredient of *Coptidis rhizoma*, is reported to have pharmacological effects such as antibacterial effects against intestinal bacteria, sedative and antispasmodic effects, anti-arteriosclerotic effects, anti-inflammatory effects, choleretic effects, and pancreatic juice secretion-stimulating effects.

As used herein, the term "extract" or "mixed extract" includes a liquid extract as it is and all possible formulations of the extract which may be produced using the liquid extract, such as a liquid extract obtained by extracting *Pinellia tuber, Zizyphi fructus, Glycyrrhiza radix, Ginseng radix, Zingiberis rhizoma, Scutellariae radix*, and *Coptidis rhizoma*, a diluted or concentrated liquid of the liquid extract, a dry product obtained by drying the liquid extract, a crude or purified product of the liquid extract, or a mixture thereof, etc. Specifically, the extract of the present invention may be used after being prepared in the form of a dry powder after extraction. In the present invention, the *Pinellia tuber, Zizyphi fructus, Glycyrrhiza radix, Ginseng radix, Zingiberis rhizoma, Scutellariae radix* or *Coptidis rhizome* may be purchased from commercially available sources or may be cultured in or collected from the wild without limitation.

In a specific embodiment of the present invention, the mixed extract of *Pinellia tuber, Zizyphi fructus, Glycyrrhiza radix, Ginseng radix, Zingiberis rhizoma, Scutellariae radix*, and *Coptidis rhizoma* may be prepared by a method of extracting respective plants and then mixing the extracts, or a method of mixing all of *Pinellia tuber, Zizyphi fructus, Glycyrrhiza radix, Ginseng radix, Zingiberis rhizoma, Scutellariae radix*, and *Coptidis rhizome*, and then extracting the mixture. The mixing process may be performed before or after extraction, and preferably, after extracting the respective plants, the mixing step may be performed, but is not limited thereto.

In the present invention, the type of extraction solvents used to extract the extracts is not particularly limited, and any solvent known in the art may be used. Non-limiting examples of the extraction solvents may include water; C1-C4 lower alcohols such as methanol, ethanol, propyl alcohol, butyl alcohol, etc.; polyhydric alcohols such as glycerin, butylene glycol, propylene glycol, etc.; and hydrocarbon solvents such as methyl acetate, ethyl acetate, acetone, benzene, hexane, diethyl ether, dichloromethane, etc.; or mixtures thereof. Preferably, the extract may be a water or C1-C4 lower alcohol extract, but is not limited thereto.

In the present invention, the method of extracting the extract is not particularly limited, and the extract may be extracted according to a method commonly used in the art. Non-limiting examples of the extraction method may include hot water extraction, ultrasonic extraction, filtration, reflux extraction, etc., and these methods may be performed alone or in combination of two or more thereof.

In a specific embodiment of the present invention, the mixed extract of *Pinellia tuber, Zizyphi fructus, Glycyrrhiza radix, Ginseng radix, Zingiberis rhizoma, Scutellariae radix*, and *Coptidis rhizome* may include a concentrate, a filtrate, a fraction, a dry product, a pulverized product, etc. which are prepared by common additional processes applicable to plant extracts, such as concentration, filtration, fractionation, drying, pulverization, etc., after extraction. In this regard, the 'concentrate' may refer to a substance in which the concentration of the main solid component is increased by removing solvents, etc. from chemicals, the 'filtrate' may refer to a substance which is obtained by separating a mixture of a liquid and a solid using a difference in the particle size, the 'fraction' may refer to a resulting product which is obtained by a fractionation method of separating a specific component or a specific group from a mixture containing various components, the 'dry product' may refer to a resulting product which is obtained by a method of removing water from a substance containing a small amount of water, and the 'pulverized product' may refer to a resulting product which is obtained by applying a force to solid particles to break them into small pieces or to cut them into small particles. In this regard, the concentrate, the filtrate, the fraction, the dry product, the pulverized product, etc. may be obtained by common methods capable of obtaining the corresponding resulting products, but are not particularly limited.

The pharmaceutical composition of the present invention may include the Banha-Sasim-Tang as described above as an active ingredient.

In this regard, the Banha-Sasim-Tang may be included at a concentration of 50 μg/ml to 800 μg/ml in the composition, but is not limited thereto. In one embodiment, the Banha-Sasim-Tang may be included at a concentration of 100 μg/ml to 700 μg/ml in the composition, but is not limited thereto. Preferably, the Banha-Sasim-Tang may be included at a concentration of 200 μg/ml to 500 μg/ml in the composition, but is not limited thereto. More preferably, the Banha-Sasim-Tang may be included at a concentration of about 300 μg/ml in the composition.

The pharmaceutical composition of the present invention may include one or more additional active ingredients in addition to the Banha-Sasim-Tang. The pharmaceutical composition of the present invention may further include a pharmaceutically acceptable carrier, excipient, or diluent commonly used in the preparation of pharmaceutical compositions, and the carrier may include a non-naturally occurring carrier.

As used herein, the term "pharmaceutically acceptable" means a feature of being non-toxic to a cell or human exposed to the composition.

Specific examples of the carrier, excipient, and diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxylbenzoate, talc, magnesium stearate, mineral oil, etc., but are not limited thereto. These compounds may be used alone or in combination of two or more thereof.

Further, the pharmaceutical composition may have any one formulation selected from the group consisting of tablets, pills, powders, granules, capsules, suspensions, solutions for internal use, emulsions, syrups, sterile aqueous solutions, non-aqueous solvents, suspensions, emulsions, lyophilized preparations and suppositories according to common methods, and may have various oral or parenteral formulations. Upon formulation, the formulation may be prepared by using a diluent or an excipient, such as a filler, an extender, a binder, a wetting agent, a disintegrating agent, and a surfactant, etc., which are generally used. Solid formulations for oral administration may include tablets, pills, powders, granules, capsules, etc., and in the solid formulation, one or more excipients, for example, starch, calcium carbonate, sucrose or lactose, gelatin, etc. may be used. Further, lubricants such as magnesium stearate, talc, etc. may be used in addition to simple excipients. Liquid formulations for oral administration may include suspensions, solutions for internal use, emulsions, syrups, etc., and may include various excipients, for example, a wetting agent, a sweetener, an aromatic agent, a preservative, etc., in addition to water and liquid paraffin which are commonly used as simple diluents. Formulations for parenteral administration may include sterile aqueous solutions, non-aqueous solvents, suspensions, emulsions, lyophilized agents, suppositories, etc. As the non-aqueous solvents and the suspensions, propylene glycol, polyethylene glycol, vegetable oil such as olive oil, injectable ester such as ethyl oleate, etc. may be used. As a base of the suppository, witepsol, macrogol, tween 61, cacao butter, laurin butter, glycerogelatin, etc. may be used, but are not limited thereto.

Another aspect of the present invention may provide a pharmaceutical composition for preventing or treating Alzheimer's disease caused by ApoE4 gene mutation, the pharmaceutical composition including the Banha-Sasim-Tang as an active ingredient.

As used herein, the term "Alzheimer's disease" refers to a degenerative brain disease that slowly develops and causes gradual deterioration of cognitive functions, including memory.

One of the causes of Alzheimer's disease is known to be the apolipoprotein E4 allele (ApoE4) gene mutation. ApoE gene is a gene that encodes the sequence of apolipoprotein E (ApoE), and the ApoE4 genotype is known to be a risk factor of developing Alzheimer's dementia. According to previous studies, it is reported that the incidence of Alzheimer's disease in those who have one APOE4 allele (heterozygous) is about 50%, and the incidence of Alzheimer's disease in those who have two alleles (homozygous) is about 91%. Furthermore, it is known that those with the APOE4 allele have an earlier onset of Alzheimer's disease.

In the present invention, the Alzheimer's disease may be Alzheimer's disease caused by ApoE4 gene mutation. In this regard, the term "Alzheimer's disease caused by ApoE4 gene mutation" may refer to Alzheimer's disease caused by the expression of ApoE4 in an individual with the ApoE4 genotype, but is not limited thereto.

The Alzheimer's disease caused by ApoE4 gene mutation may be Alzheimer's dementia caused by ApoE4 gene mutation, but is not limited thereto. In this regard, the term "Alzheimer's dementia", as used herein, refers to a dementia disease caused by Alzheimer's disease.

The Alzheimer's disease may be, for example, late onset Alzheimer's disease.

As used herein, the term "treating" means all of the actions by which symptoms of Alzheimer's disease caused by ApoE4 gene mutation have taken a turn for the better or been modified favorably by the administration of the composition.

As used herein, the term "preventing" means all of the actions by which the occurrence, progression, and recurrence of Alzheimer's disease caused by ApoE4 gene mutation is restrained or retarded using the composition.

Specifically, as an example of the above treatment, in one embodiment of the present invention, it was confirmed that phagocytosis of amyloid beta is activated for individuals with Alzheimer's disease caused by ApoE4 gene mutation, thereby suppressing the deposition of amyloid beta or removing amyloid beta.

In another embodiment, the composition of the present invention may inhibit hyperphosphorylation of tau protein in individuals with Alzheimer's disease caused by ApoE4 gene mutation.

In still another embodiment, the composition of the present invention may improve the cognitive function of individuals by promoting the phagocytosis of amyloid beta and inhibiting hyperphosphorylation of tau protein in the individuals with Alzheimer's disease caused by ApoE4 gene mutation.

As described above, it was confirmed that the composition including the Banha-Sasim-Tang of the present invention as an active ingredient has high applicability as a therapeutic composition specific to Alzheimer's disease caused by ApoE4 gene mutation.

Still another aspect of the present invention provides a method of treating Alzheimer's disease caused by ApoE4 gene mutation.

The treatment method may include the steps of examining whether or not an individual has the ApoE4 genotype, and determining, as a treatment target, the individual who is positive for ApoE4 and has Alzheimer's disease.

Further, the treatment method may include the step of administering, to an individual, the pharmaceutical composition including the Banha-Sasim-Tang as an active ingredient.

The "Banha-Sasim-Tang", "treating", "Alzheimer's disease caused by ApoE4 gene mutation", "preventing", and "administering" may be defined as described above.

Hereinbelow, the steps of the treatment method will be described in detail.

The treatment method of the present invention may include examining whether or not having the ApoE4 genotype. As used herein, the term "examining whether or not having the ApoE4 genotype" refers to examining the presence of the ApoE4 allele in the individual. The 'examining whether or not having the ApoE4 genotype' may be interpreted as having the same meaning as 'examining for ApoE4 positivity.' Since the composition to be provided by the present invention shows specific activity against Alzheimer's disease caused by ApoE4 gene mutation, it is intended to select ApoE4-positive individuals as treatment targets through the above step.

As used herein, the term "ApoE4-positive" refers to a case where an individual has at least one ApoE4 allele.

In this regard, the method of examining the presence of the ApoE4 allele may be a method commonly used in the art without limitation. The examination may be performed by an isoelectric focusing electrophoresis method, an immunological method, an immunochemical method, or a sequence analysis method, but is not limited thereto. For example, the examination may be performed by polymerase chain reaction (PCR).

The treatment method of the present invention may also include the step of determining, as a treatment target, the individual who is positive for ApoE4 and has Alzheimer's disease. In other words, the individual whose the result in the above-mentioned examination step is positive for ApoE4 and who has Alzheimer's disease may be determined as a treatment target. The treatment target may be an individual with Alzheimer's disease caused by ApoE4 gene mutation. The treatment target may be an individual with Alzheimer's disease caused by expression of the ApoE4 gene.

In this regard, the term "Individual", as used herein, refers to all animals such as rats, mice, and livestock, including humans. The animal may be not only a human, but also a mammal such as a cow, horse, sheep, pig, goat, camel, antelope, dog, or cat, etc., but is not limited thereto.

In this regard, the treatment target may be an individual having heterozygous ApoE4 genotype and suffering from Alzheimer's disease. The treatment target may be an individual having homozygous ApoE4 genotype and suffering from Alzheimer's disease. Further, the treatment target may be a patient with Alzheimer's disease induced by the expression of the ApoE4 gene.

Specifically, the treatment target may be an individual suffering from Alzheimer's dementia caused by an ApoE4 gene mutation.

The treatment method of the present invention may include administering, to the subject, the pharmaceutical composition including the Banha-Sasim-Tang as an active ingredient.

In this regard, the pharmaceutical composition may be understood as the same as the 'pharmaceutical composition for preventing or treating Alzheimer's disease caused by ApoE4 gene mutation, the pharmaceutical composition including the 'Banha-Sasim-Tang' as an active ingredient as described above.

The composition of the present invention may be administered orally or parenterally according to the desired method. When administered parenterally, external application on the skin or intraperitoneal injection, intrarectal injection, subcutaneous injection, intravenous injection, intramuscular injection or intrathoracic injection may be selected. In this regard, the term "administering" of the present invention means providing a predetermined substance to a patient by any appropriate method, and the administration route of the composition of the present invention may be administration through any general route as long as it may reach the target tissue. It may include intraperitoneal administration, intravenous administration, intramuscular administration, subcutaneous administration, intradermal administration, oral administration, topical administration, intranasal administration, intrapulmonary administration, or rectal administration, but is not limited thereto.

The administration dosage of the composition may vary depending on a patient's weight, age, gender, health status, diet, administration time, administration method, excretion rate, and severity of the disease.

Further, for the prevention and treatment of cognitive disorders, the composition of the present invention may be used alone or in combination with surgery, hormone therapy, drug therapy, and methods of using biological response modifiers. With respect to the objects of the present invention, the composition according to the present invention may be administered in combination with one or more additional drugs commonly used for Alzheimer's disease.

In the present specification, still another aspect of the present invention provides a health functional food composition for preventing or improving Alzheimer's disease, the health functional food composition including the Banha-Sasim-Tang as an active ingredient.

In this regard, one specific embodiment of the present invention provides a health functional food composition for preventing or improving Alzheimer's disease caused by ApoE4 gene mutation, the health functional food composition including the Banha-Sasim-Tang as an active ingredient.

In this regard, the terms "Banha-Sasim-Tang", "Alzheimer's disease" and "caused by ApoE4 gene mutation" may be defined as described above. Further, the weight ratio or concentration of the Banha-Sasim-Tang in the health functional food composition may be understood as being the same as defined in the pharmaceutical composition.

As used herein, the term "preventing" may be defined as described in the pharmaceutical composition, and the term "Improving" means all of the actions by which symptoms of an individual being suspected of having the disease or already developing the disease have taken a turn for the better or been modified favorably by using the composition of the present invention.

The health functional food (functional food), which is the same term as food for special health use (FoSHU), is a food prepared and/or processed using raw materials or ingredients with functional properties useful to the human body, and refers to a food having high medicinal and medical effects, which is processed to efficiently exhibit biologically modulating functions as well as to supply nutrients. Here, the term "functional" refers to obtaining a useful effect for health purposes such as regulating nutrients or physiological action for the structure and function of the human body. As described above, foods including ingredients useful to the human body, of which function and safety have been recognized by the Ministry of Food and Drug Safety, are called health functional foods. Foods that have not been approved by the Ministry of Food and Drug Safety but are considered to have beneficial effects on the human body are classified as health (supplement) foods. The food of the present invention may be prepared by methods commonly used in the art, and may be prepared by adding raw materials and ingredients commonly added in the art during preparation. In addition, the food may also be prepared in any formulation without limitation, as long as the formulation is recognized as a food.

The health food composition of the present invention may include an auxiliary agent, an additive, and other components which are acceptable for use in food without limitation, in addition to the Banha-Sasim-Tang. In this regard, the food composition of the present invention may include additional components such as medicinal herb extracts, food auxiliary additives, or natural carbohydrates, etc., in addition to the Banha-Sasim-Tang which is an essential component.

Further, the health functional food composition may further include a carrier acceptable for use in food, which may be appropriately selected and used by those skilled in the art. For example, the carrier acceptable for use in food may include various nutrients, vitamins, minerals (electrolytes), flavors such as synthetic flavors and natural flavors, etc., colorants and fillers, pectic acid and salts thereof, alginic acid and salts thereof, organic acids, a protective colloid thickener, a pH adjuster, a stabilizer, a preservative, glycerin, alcohols, a carbonating agent used in carbonated beverages, etc., but the kind is not limited to the above examples.

Further, the health functional food composition may include additional ingredients that are commonly used in food compositions to improve smell, taste, visual appearance, etc. For example, it may include vitamins A, C, D, E, B1, B2, B6, B12, niacin, biotin, folate, pantothenic acid, etc. In addition, it may include minerals such as zinc (Zn), iron (Fe), calcium (Ca), chromium (Cr), magnesium (Mg), manganese (Mn), copper (Cu), etc. In addition, it may include amino acids such as lysine, tryptophan, cysteine, valine, etc.

In addition, the health functional food composition may include food additives, such as preservatives (potassium sorbate, sodium benzoate, salicylic acid, sodium dehydroacetate, etc.), disinfectants (bleaching powder, higher bleaching powder, sodium hypochlorite, etc.), antioxidants (butylhydroxyanisole (BHA), butylhydroxy toluene (BHT), etc.), colorants (tar color, etc.), color-developing agents (sodium nitrite, etc.), bleaching agents (sodium sulfite), seasonings (MSG (monosodium glutamate), etc.), sweeteners (dulcin, cyclamate, saccharin, sodium, etc.), flavors (vanillin, lactones, etc.), swelling agents (alum, potassium D-bitartrate, etc.), fortifiers, emulsifiers, thickening agents (adhesive pastes), film-forming agents, gum base agents, antifoaming agents, solvents, improvers, etc.

Still another aspect of the present invention provides a quasi-drug composition for preventing or improving Alzheimer's disease, the quasi-drug composition including the Banha-Sasim-Tang as an active ingredient.

In this regard, one specific embodiment of the present invention provides a quasi-drug composition for preventing or improving Alzheimer's disease caused by ApoE4 gene mutation, the quasi-drug composition including the Banha-Sasim-Tang as an active ingredient.

In this regard, the terms "Banha-Sasim-Tang", "Alzheimer's disease", "caused by ApoE4 gene mutation", "preventing" and "improving" may be defined as described above. Further, the weight ratio or concentration of the Banha-Sasim-Tang in the quasi-drug composition may be understood as being the same as defined in the pharmaceutical composition.

As used herein, the term "quasi-drug" refers to an article having a milder action than drugs, among articles being used for the purpose of diagnosis, treatment, improvement, alleviation, handling, or prevention of human or animal diseases. For example, according to Pharmaceutical Affairs Law, the quasi-drugs are those, excluding articles used as drugs, including articles used for the purpose of treating or preventing human or animal diseases, which have a mild action on or have no direct influence on the human body.

The quasi-drug composition may be used by adding, as it is, the composition including the Banha-Sasim-Tang according to the present invention as an active ingredient, or may be used together with other quasi-drugs or quasi-drug ingredients, and may be appropriately used according to common methods. The mixing amount of the active ingredients may be appropriately determined depending on the purpose of use (prevention, health, or therapeutic treatment).

The quasi-drug composition may include, but is not particularly limited to, personal hygiene products, disinfectant cleaners, or ointments. The personal hygiene products may specifically include, but are not particularly limited to, toothpaste, gargles, cleaning gels, or preservatives for prosthetics such as dentures, etc.

In addition, the quasi-drug composition may be specifically prepared and used, but is not particularly limited to, in the form of ointment, lotion, spray, patch, cream, powder, suspension, gel preparation, or gel.

Still another aspect of the present invention provides use of the composition including the mixed extract of *Pinellia tuber, Zizyphi fructus, Glycyrrhiza radix, Ginseng radix, Zingiberis rhizoma, Scutellariae radix*, and *Coptidis rhizome* as an active ingredient in preventing or treating Alzheimer's disease. The Alzheimer's disease may be Alzheimer's disease caused by ApoE4 gene mutation. Further, the Alzheimer's disease may be late onset Alzheimer's disease. In this regard, the terms "Banha-Sasim-Tang", "Alzheimer's disease", "caused by ApoE4 gene mutation", "preventing", and "treating" may be defined as described above.

Still another aspect of the present invention provides use of the health functional food composition including the mixed extract of *Pinellia tuber, Zizyphi fructus, Glycyrrhiza radix, Ginseng radix, Zingiberis rhizoma, Scutellariae radix*, and *Coptidis rhizome* as an active ingredient in preventing or treating Alzheimer's disease. The Alzheimer's disease may be Alzheimer's disease caused by ApoE4 gene mutation. Further, the Alzheimer's disease may be late onset Alzheimer's disease.

Still another aspect of the present invention provides use of the quasi-drug composition including the mixed extract of *Pinellia tuber, Zizyphi fructus, Glycyrrhiza radix, Ginseng radix, Zingiberis rhizoma, Scutellariae radix*, and *Coptidis rhizome* as an active ingredient in preventing or treating Alzheimer's disease. The Alzheimer's disease may be Alzheimer's disease caused by ApoE4 gene mutation. Further, the Alzheimer's disease may be late onset Alzheimer's disease.

Advantageous Effect

A composition including Banha-Sasim-Tang of the present invention as an active ingredient and a treatment method exhibit excellent effects of reducing amyloid beta proteins and inhibiting deposition thereof, which are specific to Alzheimer's disease caused by ApoE4 gene mutation. It has high applicability as a specific therapeutic composition for Alzheimer's disease caused by ApoE4 gene mutation. In the present specification, the ApoE4-specific amyloid beta-reducing effect of the composition of the present invention was confirmed using ApoE4 human cerebral astrocytes and cerebral organoids in exemplary embodiments, and the above effects were clearly demonstrated.

In this regard, the composition and treatment method of the present invention will provide more effective customized treatment for patients with Alzheimer's disease due to the ApoE4 genotype.

BRIEF DESCRIPTION OF THE DRAWINGS

FIG. 1 shows an ApoE4 Alzheimer's dementia human induced pluripotent stem cell model which is prepared through CRISPR/Cas9 genome editing;

FIG. 2A shows a differentiation process of astrocytes, and FIG. 2B shows the fluorescence staining results of verifying differentiation of human induced pluripotent stem cells into astrocytes through neural progenitor cells and successful differentiation of astrocytes;

FIG. 3 shows a protocol for exploring the recovery of amyloid beta phagocytosis by oriental medicine-based therapeutic materials in Alzheimer's dementia astrocytes;

FIG. 4 shows the results of measuring $A\beta_{42}$ phagocytosis of ApoE3 and ApoE4 astrocytes (FIG. 4A), the recovery effect by Banha-Sasim-Tang treatment in ApoE4 astrocytes with reduced decomposition function (FIG. 4C), and the results in ApoE3 control (FIG. 4B);

FIG. 5 shows a process of preparing a dementia human induced pluripotent stem cell (APPswe) model using a CRISPR/Cas9 gene scissors technique;

FIG. 6 shows a timeline of an experiment of measuring the effect of amyloid beta phagocytosis by Banha-Sasim-Tang in APPswe astrocytes (FIG. 6A) and the results of measuring the effect of amyloid beta phagocytosis by Banha-Sasim-Tang in APPswe astrocytes (FIG. 6B);

FIG. 7 shows a progress of an experiment of exploring the effect of Banha-Sasim-Tang in ApoE4 brain organoids; and FIG. 8 shows the increased amyloid beta deposition in ApoE4 cerebral organoids and the reduction effect by Banha-Sasim-Tang, specifically, FIG. 8A shows the results of performing western blotting for examining amyloid beta, and FIG. 8B shows graphs of quantifying the above results.

DETAILED DESCRIPTION OF PREFERRED EMBODIMENTS

Hereinafter, the construction and effects of the present invention will be described in more detail with reference to Examples and Experimental Examples. However, these Examples and Experimental Examples are only for illustrating the present invention, and the scope of the present invention is not intended to be limited thereby.

Preparation Example 1: Preparation of Composition Including Banha-Sasim-Tang as Active Ingredient 1.00 g of Glycyrrhizae radix (roots and rhizomes intact of *Glycyrrhiza uralensis* Fischer, *Glycyrrhiza glabra* Linne, or *Glycyrrhiza inflata* Batal. (the family Leguminosae) or those from which periderm was removed), 0.83 g of *Zingiberis rhizoma* (dried rhizome of *Zingiber officinale* Roscoe (the family Zingiberaceae)), 1.00 g of *Zizyphi fructus* (ripe fruits of *Zizyphus jujuba* Miller var. *inermis* Rehderor *Zizyphus jujuba* Miller var. *hoonensis* T. B. Lee (the family Rhamnaceae), 1.67 g of *Pinellia tuber* (tuber of *Pinella ternata* Breitenbach (the family Araceae) from which periderm was completely removed), 1.00 g of *Ginseng radix* (roots intact of *Panax ginseng* C. A. Meyer (the family Araliaceae) or those from which small roots and cork layer were removed), 1.00 g of *Scutellariae radix* (roots intact of *Scutellara baicalensis* Georgi (the family Labiatae) or those from which periderm was removed), 0.33 g of *Coptidis rhizoma* (rhizome of *Coptis japonica* Makino, Copts *chinensis* Franchet, *Coptis deltoidea* C. Y. Cheng et Hsiao or Copts teeta Wallich (the family Ranunculaceae, from which roots were removed) were prepared. The above herbal medicines were selected and each was weighed according to the distribution of raw materials, and put in an extractor, and tap water (KP) or purified water (KP) was added in an amount of 8-10 times thereof, and extracted at 80° C. to 100° C. for 2 hours to 3 hours to prepare Banha-Sasim-Tang.

Example 1: Culture of Human Induced Pluripotent Stem Cells

An Alzheimer's dementia human induced pluripotent stem cell model with ApoE4 mutation, which is a representative genetic cause of Alzheimer's dementia, was prepared using a CRISPR/Cas9 genome editing technique (FIG. 1) and in order to use the prepared Alzheimer's dementia human induced pluripotent stem cell model in this study, ApoE3/ApoE4 isogenic induced pluripotent stem cells were cultured in a matrigel-coated 6-well plate using TeSR1 media.

As a result, the ApoE4 Alzheimer's dementia human induced pluripotent stem cell model was prepared through CRISPR/Cas9 genome editing.

Example 2: Differentiation of Astrocytes

To differentiate neural precursor cells, which are precursors of astrocytes, from human induced pluripotent stem cells, when the human induced pluripotent stem cells reached 100% confluency, they were treated with a neuronal induction medium [DMEM/F-12 GlutaMAX (Gibco), Neurobasal (Gibco), 0.5×N-2 (Gibco), 0.5×B27 (Gibco), 0.5× GlutaMAX (ThermoFisher Scientific), 5 μg/ml insulin (Sigma-Aldrich), 0.5×NEAA (Thermo Fisher Scientific), 100 μM 2-mercaptoethanol (Sigma-Aldrich), 1× Penicillin/Streptomycin (Gibco)] along with SMAD signal inhibitors, 1 μM Dorsomorphin (Tocris) and 10 μM SB431542 (Tocris) for 11 days. Further, after transferring the cells to a matrigel-coated plate, the culture medium was treated with 20 ng/ml FGF2 (Peprotech) until a rosette structure appeared.

The prepared neural precursor cells were plated at a density of $1.5\times10^5$ and then cultured in an astrocyte medium (Sciencell). The culture medium was changed every two days, and after one month of culture, the cells were detached using TrypLE (Gibco), and stained with GLAST-PE antibody (MiltenylBiotec), which is an astrocyte marker, and only GLAST-positive cells were separately collected through a flow cytometer (Sony SH800) and cultured (FIG. 2A). To verify astrocyte differentiation, fluorescence staining was performed using antibodies staining GFAP and AQP4, which are another astrocyte markers (FIG. 2B).

The differentiation of human induced pluripotent stem cells into astrocytes through neural precursor cells and the differentiation of astrocytes were verified using fluorescence staining.

Example 3: Verification of Amyloid Beta Phagocytosis in ApoE4 Astrocytes by Banha-Sasim-Tang ApoE4 astrocytes and control ApoE3 astrocytes were treated with synthetic amyloid beta ($A\beta_{42}$) together with Banha-Sasim-Tang, and after two days of culture, the amount of amyloid beta remaining in the culture medium was measured using an ELISA technique (FIG. 3).

In the case of ApoE4 astrocytes, the ability to remove $A\beta_{42}$ was significantly reduced when the culture medium was treated with $A\beta_{42}$, as compared to ApoE3 (FIG. 4A). At this time, it was confirmed that when Banha-Sasim-Tang was administered, $A\beta_{42}$ phagocytic ability increased in a concentration-dependent manner, similar to or higher than the value in the normal group, ApoE3. In particular, the removal ability under the treatment condition of 300 μg/ml significantly increased to a value higher than that of the normal group (FIG. 4C). In contrast, there was no statistically significant difference in ApoE3 astrocytes according to Banha-Sasim-Tang treatment (FIG. 4B).

Example 4: Verification of Amyloid Beta Phagocytosis in APPswe (APP Swedish) Astrocytes by Banha-Sasim-Tang Next, an APPswe astrocyte model was prepared in order to confirm whether Banha-Sasim-Tang has therapeutic activity against Alzheimer's disease caused by APPswe gene mutation. APP is an amyloid precursor protein gene and is known to be a representative causative gene of familial Alzheimer's disease.

In detail, the present applicants inserted the Alzheimer's dementia-causing mutation, APPswe (KM670/671NL double mutation of the APP gene) into human induced pluripotent stem cells of a normal person using a CRISPR/Cas9 gene scissors technique to prepare an 'Alzheimer's dementia human induced pluripotent stem cell model (APPswe)' (FIG. 5). At this time, the sequences used in this experiment are as follows.

TABLE 1

| | |
|---|---|
| WT sequence | GAGATCTCTGAAGTGAAGATGGA |
| Repair ssODN | GAGATCTCTGAAGTGAATCTCGA |

Meanwhile, the differentiation process of astrocyte cells was performed in the same manner as in Example 2. APPswe astrocytes were treated with synthetic amyloid beta ($A\beta_{42}$) together with Banha-Sasim-Tang, and cultured for two days. The amount of amyloid beta remaining in the culture medium was measured using an ELISA technique. An approximate timeline of this experiment is shown in FIG. 6A, and the results are shown in FIG. 6B.

As confirmed in the results of FIG. 6B, there was no change in the amyloid beta ($A\beta_{42}$) removal ability in APPswe astrocytes, which is a familial Alzheimer's disease line, by treatment with Banha-Sasim-Tang.

The results of Examples 3 and 4 confirmed the specific amyloid beta reduction effect of Banha-Sasim-Tang on ApoE4-bearing cells.

Example 5: Verification of Alleviation of Alzheimer's Disease-Related Pathology in Cerebral Organoids by Banha-Sasim-Tang Treatment ApoE4 cerebral organoids cultured for 4 months were treated with Banha-Sasim-Tang at a concentration of 300 μg/ml for 7 days, and then changes in the amyloid beta deposition were examined (FIG. 7).

The cultured ApoE4 cerebral organoids showed a significant increase in all lower- or higher-order polymers of amyloid beta tetramer, as compared to ApoE3 cerebral organoids. In the case of amyloid beta, it is known that, from forming a tetramer oligomer, its structure becomes different from $A\beta_{40}$ and it quickly forms a toxic nucleus, and therefore, the formation of higher-order oligomers of tetramer is a more important factor in neurotoxicity. As shown in FIG. 8B, in the group where ApoE4 cerebral organoids were treated with Banha-Sasim-Tang, a decrease in the amount of all lower- or higher-order polymers of tetramer was observed (FIG. 8B).

These results suggest that the present invention has excellent effects on amyloid beta inhibition and phagocytosis in Alzheimer's disease caused by ApoE4, and the present invention may be usefully applied to a specific therapeutic agent for Alzheimer's disease caused by ApoE4 or a specific therapeutic agent for late-onset Alzheimer's disease.

Based on the above description, it will be understood by those skilled in the art that the present invention may be implemented in a different specific form without changing the technical spirit or essential characteristics thereof. In this regard, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

The invention claimed is:

1. A method for treating Alzheimer's disease, comprising administering a pharmaceutical composition comprising, as an active ingredient, a mixed extract of *Pinellia tuber, Zizyphi fructus, Glycyrrhiza radix, Ginseng radix, Zingiberis rhizoma, Scutellariae radix*, and *Coptidis rhizoma* to a subject in need thereof, wherein the Alzheimer's disease is caused by an ApoE4 gene mutation.

2. The method of claim 1, wherein the method is for treating Alzheimer's disease of an ApoE4-positive subject.

3. The method of claim 1, wherein the Alzheimer's disease is late onset Alzheimer's disease.

4. The method of claim 1, wherein the extract is a water or C1 to C4 lower alcohol extract.

5. The method of claim 1, wherein the composition exhibits the effect of reducing amyloid beta.

6. The method of claim 1, wherein the composition is for a health functional food.

7. The method of claim 1, wherein the composition is for a quasi-drug.

* * * * *